United States Patent [19]

Light

[11] Patent Number: 4,577,337
[45] Date of Patent: Mar. 18, 1986

[54] X-RAY FLUORESCENCE TESTING OF LAMINATE STRUCTURES

[75] Inventor: Glenn M. Light, San Antonio, Tex.

[73] Assignee: Southwest Research Institute, San Antonio, Tex.

[21] Appl. No.: 612,477

[22] Filed: May 21, 1984

[51] Int. Cl.⁴ .......................................... G01N 23/223
[52] U.S. Cl. .................................... 378/044; 250/302; 378/45
[58] Field of Search ............................. 378/45, 50, 44; 250/259, 302

[56] References Cited

U.S. PATENT DOCUMENTS

| | | | |
|---|---|---|---|
| 3,351,760 | 11/1967 | Brown | 378/58 |
| 3,558,886 | 1/1971 | Carver | 250/302 |
| 3,704,370 | 11/1972 | Shelton | 378/58 |
| 4,178,513 | 1/1978 | Dubois et al. | 378/45 |
| 4,400,618 | 8/1983 | Bupp et al. | 250/302 |

Primary Examiner—Alfred E. Smith
Assistant Examiner—T. N. Grigsby
Attorney, Agent, or Firm—Gunn, Lee & Jackson

[57] ABSTRACT

An X-ray fluorescence method and apparatus of detecting subsurface impact caused delaminations and cracks in cloth and epoxy-catalyst laminates which method and apparatus permit nondestructive testing and evaluation of the existance, location, parameters and depth of the subsurface damage.

20 Claims, 1 Drawing Figure

X-RAY FLUORESCENCE TESTING OF LAMINATE STRUCTURES

BACKGROUND OF THE INVENTION

This invention relates to methods and apparatus for detecting, locating, quantifying and measuring the depth of impact caused delaminations and cracking in laminates. Such defects are particularly difficult to detect because a microscopic crack which is visually indistinguishable from other microscopic cracks on the laminate surface may be the only evidence of massive surface parallel delamination or surface perpendicular branched cracking within the laminate. The invention method and apparatus use the microscopic surface breaking cracks that are associated with impact caused subsurface delamination and cracking as a means of communicating between the surface delaminations and cracks and the laminate surface.

Laminates, often comprised of cloths of kevlar, nylon, graphite, composites or other materials, embedded with expoxy-catalyst mixtures or other bonding materials and pressed together are used in a wide variety of applications including many in which the structural integrity of the laminate is critical. Examples of such uses are containers such as filament wound kevlar-epoxy rocketmotor cases and fuel tanks. Impact damage to such laminate structures is difficult to detect, however. Delamination and cracking due to an impact can be below the laminate surface with no visible indication thereof on the surface. Moreover the subsurface damage may comprise either or both branching, surface perpendicular cracking or surface parallel delamination. The inhomogenous and layered nature of the laminate makes inspection by usual nondestructive testing methods impractical. Two-sided access is often impossible due to the geometry of particular laminate structures. Traditional sonic and ultrasonic pulse-echo NDT methods are unreliable in all but the thinnest laminate structures due to the interference caused by the numerous laminae, small air pockets and inhomogeneties inherent in laminates. Other methods including those using electrified particles, electrical capacitance, and acoustics have also been found to be inappropriate for testing hard to inspect laminates. Radiography is impractical due to the one-sided access only.

In spite of a long existing commercial need for a method and apparatus useable for testing laminate structures and numerous attempts to use known methods and apparatus for that purpose, none have solved this need until disclosure of the instant invention.

INFORMATION DISCLOSURE STATEMENT

The following patents are related to the subject matter hereof: U.S. Pat. No. 2,846,589, Aug. 5, 1958, G. E. Pellissier, et al, Apparatus for Determining the Thickness of Zinc Coating on a Ferrous Metal Base (backscatter method for measuring coatings); U.S. Pat. No. 2,939,012, May 31, 1960, S. A. Scherbatskoy, Nondestructive Testing (use of multiple sensors), U.S. Pat. No. 3,075,079, Jan. 22, 1963, A. A. Tabikh, X-Ray Fluoroscopic Analysis (analysis of specimen surfaces); U.S. Pat. No. 3,197,638, July 27, 1965, K. F. Sinclair, Backscatter Flaw Detection System (improved backscatter apparatus for flaw depth determination); U.S. Pat. No. 3,399,303, Aug. 27, 1968, S. Berk Radioactive Metal Corrosion Evaluater and Methods therefor (corrosion evalution); U.S. Pat. No. 3,417,243, Dec. 17, 1968, R. C. Hill, Method and Apparatus for X-Ray Fluorescence Gauging of a Higher Atomic Number Selected Element in a Coating on a Base (measures coating constituents); U.S. Pat. No. 3,424,902, Jan. 28, 1969, B. H. Colery, Jr., et al, Method and Apparatus for Measuring (improved hardness gauge); U.S. Pat. No. 3,511,989, May 12, 1970, Yakubovich, Device for Radiometric Determination of Elements in Test Specimens (X-ray analysis of ore and metal samples); U.S. Pat. No. 3,539,808, Nov. 20, 1970, L. K. Hahn, Measuring Corrosion on a Coated Metallic Surface by means of Back-Scattered Nuclear Radiation (corrosion evaluation); U.S. Pat. No. 2,578,722, Dec. 18, 1951, R. F. McCartney, et al, Apparatus for Determining Coating Thickness (measures coating thickness); U.S. Pat. No. 4,147,931, Apr. 3, 1979, Puumalainen, Procedure for Measuring Unit Area Weights (improved area weight measurement method); U.S. Pat. No. 4,172,224, Oct. 23 1979, Lapinski, et al, Process for the Detection of Micro-Cracks (testing of ceramics with silver nitrate).

None of the above methods are believed to be as adaptable or to give as satisfactory results for detecting, locating quantifying and determining the depth of impact caused delaminations and cracking in laminates and particularly in hard to inspect cloth/epoxy laminated materials as the invented method and apparatus nor for distinguishing surface breaking cracks which are in communication with dangerous subsurface damage from benign surface breaking cracks. The instant invention is further novel over the above patents in its use of surface breaking cracks primarily as means of communicating with subsurface damage to permit detection, location and quantification of subsurface surface parallel damage rather than as the item to be detected.

SUMMARY OF THE INVENTION

An X-ray fluorescence method and apparatus of distinguishing surface breaking cracks in cloth and epoxy-catalyst laminates which are in communication with dangerous subsurface impact caused delaminations and cracks from benign surface breaking cracks which method and apparatus permits full nondestructive testing and evaluation of the existance, location, parameters and depth of the damage. A test coating comprising a viscous medium and a penetrant containing one or more elements of high atomic number (Z) is uniformly applied to a surface of a cloth and epoxy-catalyst laminate. After an interval sufficient to allow the penetrant to penetrate any impact caused delaminations and cracks in the laminate, the test coating is removed and the laminate tested for X-ray fluorescence. Delamination and cracking to the laminate is indicated by significant X-ray fluorescence of the high Z elements. The location and surface dimensions of the damage are determined by x-y scanning, the severity of delamination and cracking is determined by quantifying the received fluorescence, and the depth of damage is determined by comparing the fluorescence attenuation for the elements of high atomic number.

Some of the advantages of the invention are its unique abilities to conveniently detect, locate, quantify and determine the depth of surface breaking defects from one side of a large range of laminate materials and structures.

An object of the invention is to provide a method and apparatus for the convenient detection, location, quantifying and determining the depth of surface breaking defects from one side of a large range of laminate materials and structures.

Another object is to provide a method and apparatus of sufficient flexibility to be useful for single or multiple purposes in different test situations and which may be used upon a variety of structures.

Another object is to provide a means of distinguishing surface breaking cracks which are in communication with dangerous subsurface damage from benign surface breaking cracks.

Further advantages and objects will be apparent to those knowledgeable in the art of materials evaluation and quality control.

DESCRIPTION OF THE PREFERRED EMBODIMENT

Figure 1:
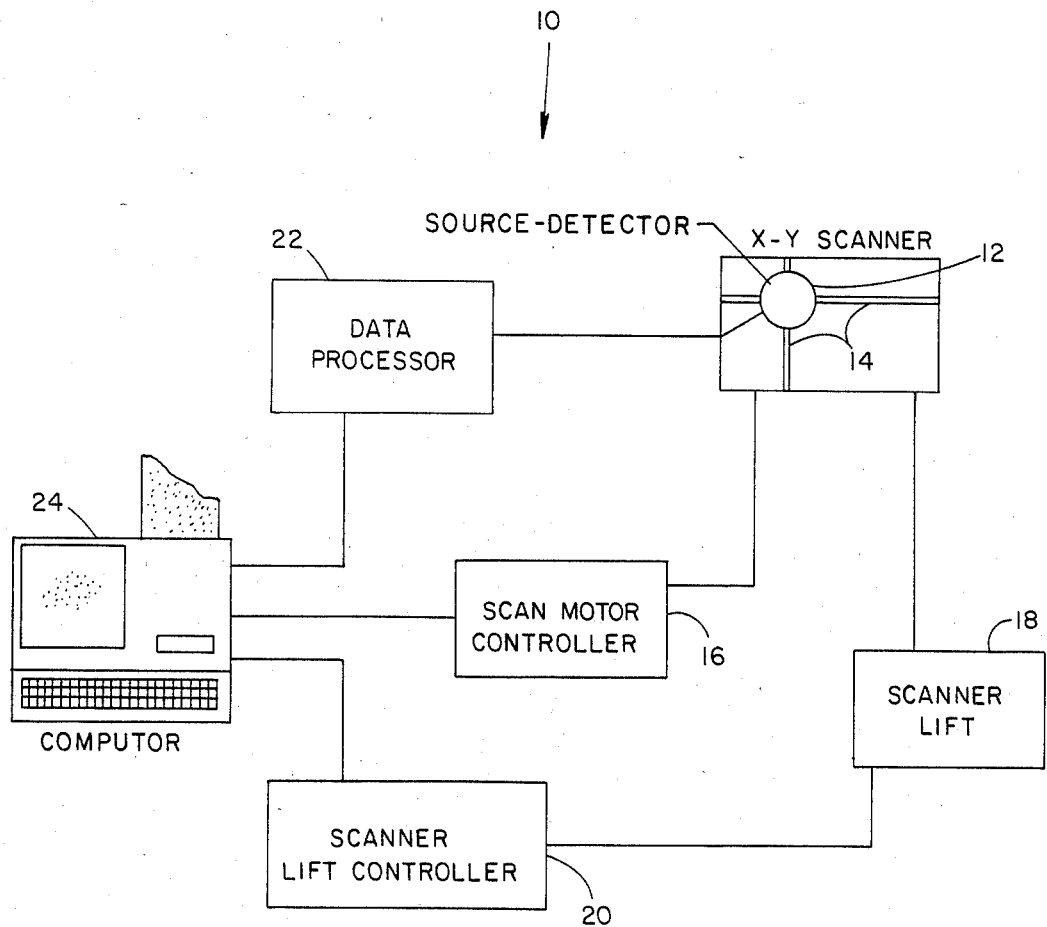
FIG. 1 is a schematic view of the invented apparatus.

The preferred embodiment and best mode of the invention for meeting the above and other objects of the invention utilizes the apparatus 10 shown in FIG. 1. A source-detector 12 is combined with an X-Y scanner 14 capable of moving the source-detector 12 in measureable desired increments. The X-Y scanner is controlled by scan motor controller 16. The X-Y scanner 14 and source-detector 12 are preferrably mounted upon a scanner lift 18 which scanner lift 18 is controlled by scanner lift controller 20.

Data obtained from the source detector 12 is processed by data processer 22 prior to communication to micro computer 24. The scan motor controller 16 and scanner lift controller 20 are preferably each controlled through the micro computer 24 for ease of operation of the apparatus 10. Upon use of the apparatus 10, therefore, the materials testing engineer may control all phases of the inspection from the console of the computer 24 while simultaneously observing the generated test date.

The source-detector 12 may employ any radioisotope source which is capable of usefully exciting the high atomic number element and any detector and counter which are capable of usefully detecting and counting the fluoresced high Z X-rays in the test specimen. The source-detector 12 is preferably a CSI 740 materials analyzer sold by Columbia Scientific Industries Corp. When the CSI 740 is used, its standard Surface Probe is the source-detector 12 preferably used. Although the element range of this particular probe is from aluminum (atomic number 13) through uranium (atomic number 92), this range can be usefully exceeded on either end of the spectrum if other source-detector probes are used. Several readily available X-ray sources can be used within the source-detector 12 such as iron ($FE^{55}$), curium ($CM^{244}$), cadmium ($CD^{109}$) and americium ($AM^{241}$). As will be discussed below the choice of the proper X-ray source will depend upon the high atomic number elements used with the penetrant in the invention. The preferable source is either cadmium $CD^{109}$ or americium $AM^{241}$ for exciting zirconium (Zr) deposited in the damaged laminate during the detection process. The source-detector 12 indicates localized X-ray intensity by outputing signals in the Zr channel which have been corrected for background using background subtraction techniques.

The x-y scanner 14 is a two axis positioning mechanism driven by one or a combination of stepper motors or other controllable motors. For simple curved test surfaces, one axis of motion preferably follows a curved track which conforms to the curvature of the test surface. The invention preferably uses one of two methods to solve the problem of changing radius and compound curvatures encountered on irregular test surfaces due to attachment parts, portholes, outlets, etc. In the first method, the requisite constant distance of the source-detector 12 from the test surface is maintained by using a surface following cart with soft rubber tires to carry the source-detector 12 and x-y scanner 14. The second method uses a third driven axis (in the z plane) which maintains the constant distance either by responsiveness to a scanner to surface measuring device or by programming to follow the compound curves.

The micro computer 24 is preferably a HP-85 desk top micro computer manufactured by Hewlett-Packard Company. The HP-85 micro computer is preferred because it combines the processor, key board, CRT display, printer and cassette drive in a single convenient package. The micro computer 24 preferably communicates with the scan motor controller 16, scanner lift controller 20 and data processor 22 through an inner face bus such as the IEEE-488(HP-IB) inner face bus manufactured by Hewlett-Packard Company. Programs for directing the scanner lift 18 to cause the source-detector 12 to follow test specimen surface curves are preferably loaded and used with the micro computer 24. A variation of the above apparatus which may be useful in some circumstances is the use of one or more X-ray photographs (radiographs) to either initially detect or subsequently confirm and quantify a defect.

To prepare a test surface for testing by the above apparatus, a test coating comprised of a relatively viscous medium and a penetrant containing at least one high atomic number (Z) element is applied uniformly to the surface of the test specimen. After a sufficient period of time (dependent upon the test surface and upon the test coating used), the surface is wiped clean of the test coating. The preferable time interval for leaving the test coating on the laminate surface is 30 minutes and may range from 10 minutes to 2 hours although lesser or greater intervals may also give useable results. The apparatus 10 is then used to test the specimen for X-ray fluorescence usually of the highest Z element. Detected X-ray fluorescence which is localized and is significantly greater than the average X-ray fluorescence background for the test specimen indicates the presence of a possible defect. An X-ray fluorescence reading is deemed to be significant and to indicate a possible defect when it is sufficiently greater than the average X-ray fluorescence background to stand out from the background. In applications where quantification is useful or necessary the background may be measured and given an arbitrary value such as zero, the background average fluctuations observed as interference and any fluorescence readings having at least a 2 to 1 ratio over the interference deemed significant. Such a system further permits quantification of the volume of voids in the cracking and delamination in any test cell of the laminate, the larger the fluorescence reading to interference ratio the larger the volume of voids in that cell. As most laminates are covered with an impermiable outer surface layer the background interference will typically be approximately the same before application of the test coating and after its removal. As a precaution, however, calibration of background interference should be accomplished both before application of the test coating and after its removal as some laminate outer surface will have different test coating absorbtion qualities. Due to the disclosed arrangement of the apparatus 10, upon moving the source-detector 12 along and adjacent to the surface the X-ray fluorescence data can be correlated with the location of the source-detector 12 on the test specimen where the excessive fluorescence occured. This is identified as indicating the location of a possible laminate defect. In contract to surface breaking cracks which are in communication with dangerous subsurface damage, benign surface breaking cracks will typically be extremely localized and often have significant fluorescence.

The use of the micro computer 24 controlled x-y scanner 14 incrementally moves the source-detector 12 in a scan pattern preferably 24×24 inches square while maintaining the source-detector 12 a constant distance, preferably $\frac{1}{8}$ to $\frac{1}{4}$ inch, from the laminate being tested. Other scan patterns and distances may also be used. The 0.5×0.5 inch aperture of the source-detector 12 is preferably allowed to dwell for approximately 1.6 second over each target cell to accumulate X-ray counts. It is understood that the aperture size may be decreased or the source-detector 12's dwell time over each taget cell may be increased to increase the tests' specificity and that the aperture size may be increased or the source-detector 12's dwell time over the target cell may be decreased to shorten the tests' duration. After subtraction of the background fluorescence, the micro computer 24 presents the accumulated data from the scan in a two dimensional image of the tested area. The amount and location of the remaining fluorescence is preferably indicated by dividing the area scanned into cells and using numbers scaled from 0 to 9 (or any other ranking system) to indicate received fluorescence. A graphic display may also be printed for hard copy retention.

The preferred significant fluorescence value for indicating detection of a defect when this ranking system is used is 3 although the arbitrary nature of system permits different calibration values to be used. The preferred method of group significant fluorescence values for the purpose of localizing the detected defect is to assume that all readings of greater than 2 which are adjacent to significant values (3 or more) or are adjacent to other readings of 2 or more which are directly or indirectly (through other cells of readings in excess of 2) adjacent to cells having significant fluorescence values indicate the location of part of the defect.

The penetrant may be any low viscosity and low surface tension fluid which is miscible with the chosen element of high atomic number, is capable of penetrating surface breaking cracks in the laminate and carrying the element of high atomic number into the cracks and subsurface delaminations. The penetrant preferably has a viscosity of one centipose or less and a surface tension of 20 dynes/cm or less. A further limitation on the penetrant is that it should not dissolve either the resin-catalyst bonding material or the material such as kevlar which forms the composite laminate under inspection. For the trace element zirconium and a test laminate specimen of kevlar, for example an organic solvent, octoate, was discovered to be the most useful such penetrant. Zirconium octoate is a clean colorless liquid which does not interfere with the X-ray spectrum of the zirconium trace elements and does not desolve kevlar or its resin-catalyst bonding material. The preferable zirconium octoate solution is six percent zirconium with useful solutions ranging from as low as 3 percent zirconium to as high as 15 percent zirconium.

The high atomic number element may be any trace element of an atomic number sufficiently greater than the greatest atomic number element present in the laminate itself to be easily identifiable by the chosen X-ray source detector. Preferable such trace elements for the invented test are zirconium, zinc, barium, lead, and uranium. While each of these trace elements is useable when combined with an appropriate penetrant, for example, zinc bromide, barium sulfate, lead nitrate and uranyl nitrate; zirconium octoate is preferably used due to its lower surface tension and consequent better penetrability. Further barium sulfate was found to be too powdery to effectively enter certain laminates while the lead nitrate solution, though effective, is poisonous and not as suitable for future use by untrained technicians.

A viscous medium is useful in maintaining the penetrant upon the laminate surface where the volatility of the penetrant causes rapid evaporation and/or where the slope of the laminate surface creates difficulties in maintaining a uniform coating of the penetrant upon the laminate surface due to gravity. This is particularly true since surface breaking cracks in the laminate will soak up amounts of the penetrant immediately adjacent to the cracks and the test's reliability is dependent upon equal accessible amounts of the penetrant being uniformly available over the entire test surface during this part of the test. The term "surface breaking cracks" and surface breaking defects as used herein are not limited to cracks or defects which open to the surface of the specimen, but also includes any cracks or anomalies which, while apparently covered by an outer surface layer, are sufficiently close to permeable or invisably damaged or defective portion of the outer surface to allow communication of the penetrant from the surface to the crack or anomaly. If the reservoir of penetrant adjacent to the surface breaking crack is exhausted prior to the end of the predetermined interval for leaving the penetrant upon the laminate surface, the test function of permitting a uniform flow of penetrant into the laminate's cracks during the test interval will have been defeated. Mediums which are relatively more viscous and less volatile than the penetrant may, therefore, be usefully mixed with the penetrant to form a test coating which may be more conveniently and usefully applied than the penetrant alone. The viscous medium is preferably miscible with the chosen penetrant and radio-opaque in the relevant X-ray spectra regions. While gels and Cab-O-Sil are useful such viscous mediums, a parifin solution is the medium preferably used.

It should be recalled that the viscous medium is not necessary for all uses of the invented test method.

Alternative methods of uniformly applying the test mixture to the laminate are by spraying it on, applying it with a viscous medium such as a gel, or applying it in a fibrous sponge-like element which is held or strapped to the laminate surface.

To determine the depth of the defect, two high atomic number (Z) elements of sufficiently different X-ray spectra are used to prevent overlapping of main intensity spectral lines. If, for example, zirconium is used as the first trace element, copper may be used as the second trace element. The first and second trace elements may either be combined and applied together with a single penetrant or the second trace element may be applied subsequently. Because the X-ray spectra lines of zirconium and copper are different, and the attenuation rates for their X-ray spectra are known, the received peaks of the zirconium and copper spectra may be measured to determine the attenuation of the copper peak relative to the zirconium peak. Because attenuation is a function of distance in the structure and the particular trace element, knowledge of the relative initial amounts of the first and second trace elements in the test mixture and measurement of their fluorescence from the detected defect permit the depth of the defect to be mathematically determined.

Fibrous laminate composites are the items most usefully tested with the invented method as impacts which are sufficiently severe to cause significant damage normally cause microscopic cracking of the epoxy-catalyst bonding material layered upon the surface of the laminate together with further subsurface cracking. It has been found that microscopic surface cracking which is invisible to the naked eye will still permit sufficient penetrant to reach subsurface delaminations to provide useful test results due to capillary action. In actual testing with penetrants containing visible dyes it has been confirmed by disection of the test laminate that communication of the penetrant within the test specimen follows the subsurface debond and delamination zones within the laminate that are caused by surface impact.

Although subsurface delamination is structurally significant damage it is a difficult type of damage. This is particularly true with respect to delaminations occurring many lamina below the outer surface.

"Subsurface cracks" as used herein refers to cracking or branching from one or more points located below the laminate surface. While subsurface cracks in a laminate communicate to the surface via surface breaking cracks they begin at lamina beneath the surface.

EXAMPLE

A uniform thin layer of zirconium octoate solution (6% zirconium) was placed upon a horizontal, planar impact damaged filament wound kevlar epoxy case and allowed to stand for 30 minutes. The surface of the case was wiped clean and was then tested using both a laboratory X-ray fluorescence analyzer using an X-ray potential of 29 kilovolts and a tube current of 32 microamperes and a CXI 740 materials analyzer with a $Cd^{129}$ source. The time count per inch square was 20 seconds. Experimental X-ray fluorescence intensity results correlated with a subsequent destructive assay of the case for detecting, locating and quantifying the impact caused cracks and delaminations in the case. No cracks or delaminations of any consequence were found by the destructive assay which had not been previously located using the invented method.

While the invention has been described in connection with the preferred embodiment, it is not intended to limit the invention to the particular form set forth, but, on the contrary, is intended to cover such alternatives, modifications and equivalents as may be included within the spirit and scope of the invention as defined by the appended claims.

What is claimed is:

1. An X-ray fluorescence test method for detecting, locating and quantifying impact caused delaminations and subsurface cracks in a laminate with an X-ray fluorescence source-detector comprising:

placing a substantially uniform layer of a test coating on the surface of a test portion of said laminate, said test coating being comprised of a penetrant of low viscosity and low surface tension which is capable of penetrating the surface breaking cracks associated with impact caused delaminations and subsurface cracks in said laminate and at least one element of high atomic number (Z) which is detectable by said X-ray fluorescence source-detector;

leaving said test coating upon said surface for a sufficient period of time to allow said penetrant to penetrate said delaminations and subsurface cracks and carry sufficient amounts of said high atomic number (Z) element into said delaminations and cracks to be detectable by said X-ray fluorescence source-detector after said test coating is removed from said surface;

removing said test coating from said surface;

testing said test portion of said laminate with said X-ray fluorescence source-detector for significant X-ray fluorescence;

detecting said delaminations and subsurface cracks, if any, by using any said significant X-ray fluorescence as an indication of a delamination or crack in said test portion;

locating said delaminations and subsurface cracks by moving said X-ray fluorescence source-detector along said surface of said test portion, observing which areas emit significant X-ray fluorescence and using said significant X-ray fluorescence from any given area of said surface as an indication that a said delamination or subsurface cracking is located in said area; and quantifying said delamination and subsurface cracking by determining the boundaries of said delaminations and subsurface cracks by moving said X-ray fluorescence source-detector to locate the parameters of said significant X-ray fluorescence and deeming said significant X-ray fluorescence parameters to be the boundaries of said delaminations and subsurface cracks and by determining the severity of said delaminations and subsurface cracks by measuring the intensity of said X-ray fluorescence from said delaminations and subsurface cracks and deeming the relative intensity of said X-ray fluorescence to be indicative of the relative severity of said delaminations and subsurface cracks.

2. The method of claim 1 wherein said test coating further comprises a medium which is of significantly greater viscosity than said penetrant, is substantially radio-opaque in the X-ray spectra region of said first element of high atomic number (Z) and is capable of maintaining said substantially uniform coating of said penetrant upon said laminate surface for a longer period of time than would be practical using said penetrant alone.

3. The method of claim 1 further comprising determining the depth of said delamination or subsurface cracking by using a second element of high atomic number (Z) in said test coating which second element is capable of being detected by said X-ray fluorescence source-detector and distinguished from said first element by said X-ray fluorescence source-detector, measuring the attenuation of said second element's detected fluorescence relative to said first element's fluorescence and using said difference in attenuation to determine said delamination's or subsurface cracking's depth.

4. The method of claim 3 wherein said second element of high atomic number is copper.

5. The method of claim 3 wherein said test coating further comprises a medium which is of significantly greater viscosity than said penetrant substantially, is radio-opaque in the X-ray spectra region of said first element of high atomic number (Z) and is capable of maintaining said substantially uniform coating of said penetrant upon said laminate surface for a longer period of time than would be practical using said penetrant alone.

6. The method of claims 2 and 3 wherein said X-ray fluorescence source-detector is connected to an x-y scanner which is controllable by an x-y scanner controller and is moveable to said test portion of said laminate by means of a scanner lift, said scanner lift is controlable by a scanner lift controller, said X-ray fluorescence source-detector and x-y scanner are in communication with a data processor and said data processor is in communication with a display unit, said method further comprising:
remotely controlling the movement of said X-ray fluorescence source-detector to, along and from said test portion of said laminate;
displaying said X-ray fluorescence received by said X-ray fluorescence source-detector and;
correlating said display of received X-ray fluorescence with corresponding x-y scanner positions by means of said data processor and displaying said received X-ray fluorescence to x-y scanner position data upon said display unit.

7. The method of claim 6 further comprising calibrating said test method by testing said test portion of said laminate with said X-ray fluorescence source-detector for X-ray fluorescence prior to placement of said test coating on said test portion, averaging the X-ray fluorescence received per unit of test portion surface, using said average X-ray fluorescence per unit as the measure of background X-ray fluorescence and subtracting said X-ray fluorescence background from said received X-ray fluorescence to facilitate detection, location and quantification of delamination and cracks.

8. The method of claim 7 further comprising consolidating the control and display portions of the test method by controlling said scan motor controller said scanner lift controller and said data processor by means of a computer connected to said scan motor controller and said scanner lift controller and displaying said processed X-ray fluorescence and x-y scanner data at said computer.

9. The method of claim 8 wherein said penetrant is an organic solvent which does not substantially dissolve either the bonding material or the fibrous material of said laminate, has a viscosity of less than 1 centipose, a surface tension of less than 20 dynes/cm., is substantially radio-opaque in the X-ray spectra region of said first element of high atomic number (Z) and is mixable with said first element of high atomic number.

10. The method of claim 9 wherein said penetrant and first high atomic number (Z) element mixture is zirconium octoate.

11. The method of claim 9 wherein said testing is of a curved laminate surface by means of an x-y scanner mounted upon a surface following device.

12. The method of claim 9 wherein said testing is of a curved laminate surface by means of an x-y scanner having a third driven axis which maintains a substantially constant distance between said X-ray fluorescence source-detector and said curved laminate surface.

13. The method of claim 9 wherein said testing is of a curved laminate surface by means of an x-y scanner having an axis which conforms to said laminate curvature.

14. A test unit for X-ray fluorescence detecting, locating and quantifying impact caused delaminations and subsurface cracking in a laminate comprising:
an X-ray fluorescence source-detector connected to an x-y scanner capable of moving said x-y fluorescence source-detector relative to said laminate;
a scan motor controller connected to said x-y scanner capable of controlling said x-y scanner;
a data processor connected to said X-ray fluorescence source-detector and said x-y scanner capable of processing and correlating data received from said X-ray fluorescence source-detector and said x-y scanner;
a data display unit connected to said data processor capable of displaying information produced by said data processor;
a computer connected to said data display unit and said scan motor controller capable of controlling said data display unit and of remotely controlling said scan motor controller;
a test coating for substantially uniform placement on said laminate, said test coating comprised of a penetrant capable of penetrating the surface breaking cracks associated with impact caused delaminations and subsurface cracking in said laminate, a sufficient concentration of a first element of sufficiently high atomic number to be detectable by said X-ray fluorescence source-detector if carried by said penetrant into impact caused delaminations and subsurface cracking and a medium of significantly greater viscosity than said penetrant which is substantially radio-opaque in the X-ray spectra region of said first element of high atomic number and capable of maintaining said substantially uniform test coating on said laminate for a longer period of time than would be practical using said penetrant alone.

15. The test unit of claim 14 wherein said unit is additionally capable of detecting and distinguishing a second element of high atomic number, of comparing the attenuation of said second element relative to the attenuation of said first element and of therefrom determining and displaying information relating to the depth of delamination and subsurface cracking in said laminate and wherein said test coating further comprises a sufficient concentration of said second element of sufficiently high atomic number to be detectable by said X-ray fluorescence source-detector if carried by said penetrant into a delamination and subsurface cracking of said laminate and which is sufficiently different in atomic number than said first element to be distinguishable from said first element by said X-ray fluorescence source-detector.

16. The test unit of claim 14 wherein said x-y scanner is connected to a scanner lift which is capable of lifting said x-y scanner, to, along and from said laminate, said scanner lift is controlled by a scanner lift controller and said scanner lift controller is remotely controllable from said computer and wherein said X-ray fluorescence source-detector, x-y scanner, scan motor controller, data processor, data display unit and computer are in sufficient communication to permit display of received X-ray fluorescence to x-y scanner position data upon said display unit to facilitate quantification of said delaminations and subsurface cracking.

17. The method of claim 16 wherein said penetrant is an organic solvent which does not substantially dissolve either the bonding material or the fibrous material of said laminate, has a viscosity of less than 1 centipose, a surface tension of less than 20 dynes/cm., is substantially radio-opaque in the X-ray spectra region of said element of high atomic number (Z) and is mixable with said element of high atomic number.

18. The test unit of claim 16 wherein an x-y scanner is mounted upon a surface following device for testing a curved laminate surface.

19. The test unit of claim 16 wherein said x-y scanner has a third driven axis which maintains a substantially constant distance between said X-ray fluorescence source-detector a curved laminate surface.

20. The test unit of claim 16 wherein said x-y scanner has an axis which conforms to a curved laminate surface.

* * * * *

UNITED STATES PATENT AND TRADEMARK OFFICE
CERTIFICATE OF CORRECTION

PATENT NO. : 4,577,337
DATED : March 18, 1986
INVENTOR(S) : Glenn M. Light

It is certified that error appears in the above—identified patent and that said Letters Patent is hereby corrected as shown below:

Column 1, after line 5 insert the following new paragraph:

The government has a paid-up license in this invention and the right in limited circumstances to require the patent owner to license others on reasonable terms as provided for by the terms of Contract No. N0003 081C0081 awarded by the Strategic System Profject Office, Department of the Navy.

Signed and Sealed this

Sixteenth Day of June, 1992

*Attest:*

DOUGLAS B. COMER

*Attesting Officer*   Acting Commissioner of Patents and Trademarks